United States Patent [19]
O'Brien et al.

[11] Patent Number: 5,757,481
[45] Date of Patent: May 26, 1998

[54] METHOD FOR TESTING A TURBIDITY SENSOR

[75] Inventors: Gary R. O'Brien; Alan V. Sheriff, both of Freeport, Ill.

[73] Assignee: Honeywell Inc., Minneapolis, Minn.

[21] Appl. No.: 560,050

[22] Filed: Nov. 17, 1995

[51] Int. Cl.$^6$ ............................................. G01J 1/02
[52] U.S. Cl. .................. 356/243; 250/573; 250/575; 250/576; 356/440; 356/441; 356/442
[58] Field of Search ..................... 356/243, 341, 356/72, 158, 103, 442, 440, 441; 600/745; 250/573, 575, 576

[56] References Cited

U.S. PATENT DOCUMENTS

| | | | |
|---|---|---|---|
| 3,892,485 | 7/1975 | Merritt et al. | 356/103 |
| 4,291,980 | 9/1981 | Patterson | 356/243 |
| 5,059,811 | 10/1991 | King | 250/573 |
| 5,291,626 | 3/1994 | Molnar et al. | 8/158 |
| 5,444,531 | 8/1995 | Foreman et al. | 356/341 |
| 5,446,531 | 8/1995 | Boyer et al. | 356/72 |

OTHER PUBLICATIONS

Booklet Titled "Turbidity Standards" by Clifford C. Hach, 1985.

*Primary Examiner*—Frank Gonzalez
*Assistant Examiner*—Michael P. Stafira
*Attorney, Agent, or Firm*—William D. Lanyi

[57] ABSTRACT

A method is provided to test turbidity sensors using a solid block that is particularly formulated to have a predetermined turbidity value. The solid block, which is partially transparent, is made by mixing calcium carbonate with a clear acrylic. A plurality of sample sensors are selected to be used as an intermediate standard to correlate the results achieved when the block is tested to results that would be achieved if liquid turbidity samples are tested. The six sample sensors are used to measure the turbidity of a plurality of liquid samples. The six sample sensors are then used to test the solid block in order to make sure that the turbidity represented by the solid block is within an acceptable range that is normally dictated by either a national standard or a particular customer requirement. Each of the plurality of sample sensors is used to test the solid block a plurality of times to form an average ratio value that can be used as a first representative magnitude for each of the sample sensors. After ignoring the highest and lowest magnitude from the sample sensors, the remaining magnitudes are averaged to achieve a second representative magnitude that can be used in comparison to actual results achieved during production testing.

10 Claims, 6 Drawing Sheets

METHOD FOR TESTING A TURBIDITY SENSOR

BACKGROUND OF THE INVENTION

1. Field of the Invention

The present invention relates generally to a method for testing a turbidity sensor and, more particularly, to a method which utilizes a solid block of material which has been specifically manufactured to have a predetermined turbidity value so that it can be disposed between a light transmitting component and a light receiving component of a turbidity sensor.

2. Description of the Prior Art

Many different types of turbidity sensors are well known to those skilled in the art. Sensors of this type find use in many different types of applications, such as lubrication systems, clothes washers and dishwashers.

U.S. Pat. No. 3,892,485, which issued to Merritt et al on Jul. 1, 1975, discloses a monitoring apparatus for measuring particles that are suspended in liquid and also for measuring the opacity of the liquid. The system relates to a portable monitoring apparatus for detecting wear particles that may be suspended in a liquid such as the lubricating oil of turbine engines and for detecting changes in the opacity of the oil. The oil sensor may be inserted directing into the lubrication system of the engine and consists of a sensor assembly having a chamber or U-shaped channel into which the oil flows. A light source and a first photodiode are positioned on opposite sides of the channel so that the photodiode measures the attenuation of the light passing through the oil. A second photodiode is placed at a 90 degree angle to the light beam to measure light scattered by wear particles suspended in the oil. The signals from the two photodiodes are processed and displayed to provide an indication of the degree of attenuation of the light beam due to changes in opacity and of the magnitude of the scattered light which is a measure of the amount of wear debris in the oil. The opacity of the oil is measured without directly sensing the degree of light attenuation. That is, illumination of the scatter field of view and of the first photodiode is kept constant by varying the light emission from the lamp through a closed loop control system. The change in the lamp supply voltage necessary to maintain the illumination level constant is thus a measure of the light attenuation due to changes in opacity. Furthermore, by maintaining a constant illumination level in the scatter field of view, errors in the scatter output indication are avoided. That is, in the absence of a constant light level in the scatter field of view, the amount of light scattered by a given concentration of particles varies with the opacity of the oil. As opacity increases, attenuation increases the scattered light decreases. This results in decreased output from the scatter photodiode giving an erroneous indication that there has been a reduction in the particle concentration, whereas the actual reduction of the output from scatter photodiode is due to the darkening color of the oil. By maintaining constant illumination in the scatter field of view through a closed control loop which varies the light output of the lamp, an accurate measurement of the particle concentration is made possible by eliminating errors which are brought about by changes in the opacity of the oil.

U.S. Pat. No. 5,291,626, which issued to Molnar et al on Mar. 8, 1994, discloses a machine for cleansing articles, such as a dishwasher, that incorporates a device for measuring the turbidity of a liquid which is at least partially transparent. The device includes a sensor for detecting scattered electromagnetic radiation, regardless of polarization, and a sensor for detecting transmitted electromagnetic radiation, regardless of polarization.

U.S. Pat. No. 5,446,531, which issued to Boyer et al on Aug. 29, 1995, describes a sensor platform for use in machines for washing articles. A plurality of fluid condition sensors are combined together to provide a sensor cluster that senses turbidity, temperature, conductivity and the movement of a ferromagnetic object. The sensors are attached to a substrate and encapsulated, by an overmolding process, with a light transmissive and fluid impermeable material. The sensor cluster can be disposed at numerous different locations within a body of fluid and does not require a conduit to direct the fluid to a particular location proximate the sensor. In a preferred embodiment of this device, a circuit is provided which monitors the signal strength of first and second light sensitive components to determine the turbidity and, in addition, those signal strengths are also use to advantageously determine the most efficient magnitude of current necessary to drive a light source, such as a light emitting diode. By controlling the current to a light emitting diode as a function of the strength of light signal received by first and second light sensitive components, the turbidity sensor can be operated at a more efficient and effective level. It has been found that a sensor platform such as the one described in U.S. Pat. No. 5,446,531, can best be utilized by disposing the sensor platform within the pump housing of the machine for washing articles, such as a dishwasher.

U.S. Pat. No. 5,444,531, which issued to Foreman et al on Aug. 22, 1995, describes a sensor with LED current control for use in machines for washing articles. In one application of the turbidity sensor, a circuit is provided to monitor the signal strength of first and second light sensitive components in order to determine turbidity and, in addition, those signal strengths are also used to advantageously determine the most efficient magnitude of current necessary to drive a light source, such as a light emitting diode. By controlling the current to a light emitting diode as a function of the strength of a light signal received by first and second light sensitive components, the turbidity sensor can be operated at a more efficient and effective level.

To facilitate mass production of turbidity sensors, it is necessary to assure that each turbidity sensor will operate in a manner that is generally similar to all other turbidity sensors of the same style which are made for the same type of application. Mass production requires this type of interchangeability between individually manufactured components such as turbidity sensors. When turbidity is measured, as part of a testing or calibration procedure, a well known technique involves the mixture of a powder with a liquid such as water, in preselected proportions, to create a liquid that has a precisely determined turbidity. The liquid is then used in conjunction with a turbidity sensor to determine whether or not the turbidity sensor reads the correct turbidity value, generally measured in nephalometric turbidity units or NTU's. In other words, disposing a turbidity sensor into a container filled with a mixture of powder and water allows the turbidity sensor to be tested to determine if it provides an appropriate signal that accurately represents the turbidity of the prepared solution. One well known technique involves the use of Formazin suspended in water and used as a reference for turbidity or opacity. Formazin is the condensation polymer of hydrazine sulfate and hexamethylenetetramine. Liquid solutions of this type can be used in several ways to test turbidity sensors. If the turbidity sensor is the immersion type of transducer, it can be disposed in a container of the liquid. Alternatively, if the turbidity sensor is a flow through type of device, a prepared solution of Formazin can be caused to flow through the sensing region of the sensor.

U.S. Pat. No. 4,291,980, which issued to Patterson on Sep. 29, 1981, describes several different types of turbidity measurement techniques, including the use of Formazin mixed with water. This patent describes a styrene-divinylbenzene copolymer and its method of manufacture. In describing the copolymer, which has been accepted as a standard in the measurement of turbidity in water, this patent also discusses the history of turbidity measurement and describes several techniques for measuring the turbidity of a fluid.

A booklet titled "Turbidity Standards" by Clifford C. Hach has been published for the purpose of describing the historical development of turbidity measurements, the development of turbidity standards, the use of Formazin standards and the use of certain secondary standards. This booklet is published by the Hach Company and identified as booklet number 12 of the Technical Information Series. This turbidity standard booklet, U.S. Pat. No. 5,444,531, U.S. Pat. No. 5,446,531, U.S. Pat. No. 5,291,626 and U.S. Pat. No. 3,892,485 are all explicitly incorporated by reference in this description of the present invention.

Known techniques for measuring turbidity typically require the use of a liquid that has been formulated to have a preselected turbidity. In most applications, the preselected turbidity is achieved by mixing Formazin and water in precise proportions to achieve the desired turbidity as measured in nephalometric turbidity units (NTU's) or Formazin turbidity units (FTU's). One disadvantage of this type of turbidity measurement is the requirement that a liquid solution be used during the testing or calibration process. If turbidity sensors are mass produced, the necessity of immersing each turbidity sensor into a liquid bath to test its turbidity could significantly increase the overall manufacturing costs of the turbidity sensor. If, on the other hand, a simpler testing and calibration method is used, that simplified method might not be appropriately traceable to an accurately determined turbidity such as the well known and accepted processes typically employed by those skilled in the art. It would therefore be significantly beneficial if a mass production testing method could be developed that quickly and accurately determines the accuracy of operation of a turbidity sensor without requiring the sensor to be immersed in a bath of liquid.

SUMMARY OF THE INVENTION

The present invention relates to a method for testing a turbidity sensor in such a way that the testing process can be quickly and efficiently performed and which is traceable to known and accepted turbidity standard processes. The method of the present invention comprises the step of providing a solid block of material that has a preselected turbidity. The block is disposed between a light source of a turbidity sensor and a first light sensitive component of the turbidity sensor. The turbidity sensor is then activated in order to provide an output signal which is representative of the turbidity of a medium disposed between the light source and the first light sensitive component. An output signal is received from the turbidity sensor and is compared to a predetermined range of values. Based on the comparison, the present invention determines the acceptability of the turbidity sensor based on whether its output signal magnitude and its relationship to the predetermined range of values.

In one particular embodiment of the present invention, the preselected turbidity of the solid block is determined by measuring the turbidity of the solid block with several sample sensors that are chosen as standard reference sensor for the purpose of these testing steps. This characterizing step can be accomplished by selecting a plurality of sample sensors and then disposing the solid block between the light source and the first light sensor component of each of the sample sensors. Each of the sample sensors is activated to provide the output signal for each of the sample sensors. The output signal is received for each of the sample sensors and a plurality of first representative magnitudes of the output signal is determined for each of the sample sensors. Next, a second representative magnitude is calculated as a function of the plurality of first representative magnitudes and, in addition, a predetermined range of acceptable values is calculated as a function of the second representative magnitude.

In certain applications of the present invention, the method comprises providing a plurality of liquid samples wherein each of the liquid samples is of a measurable different turbidity than the other of the plurality of liquid samples. The turbidity of each of the plurality of liquid samples is measured with each of the sample sensors prior to performing the characterizing step.

The turbidity sensor that is tested by the present invention can comprise a second light sensitive component. In turbidity sensors that comprise two light sensitive components, the light sensitive components can be disposed at positions to receive light transmitted directly from the light source and to receive light scattered by particulates in the medium being measured. However, it should be clearly understood that the method of the present invention is equally applicable to turbidity sensors that use a single light sensitive component.

BRIEF DESCRIPTION OF THE DRAWINGS

The present invention will be more fully and completely understood from a reading of the Description of the Preferred Embodiment in conjunction with the drawings, in which.

DESCRIPTION OF THE PREFERRED EMBODIMENT

Figure 1:
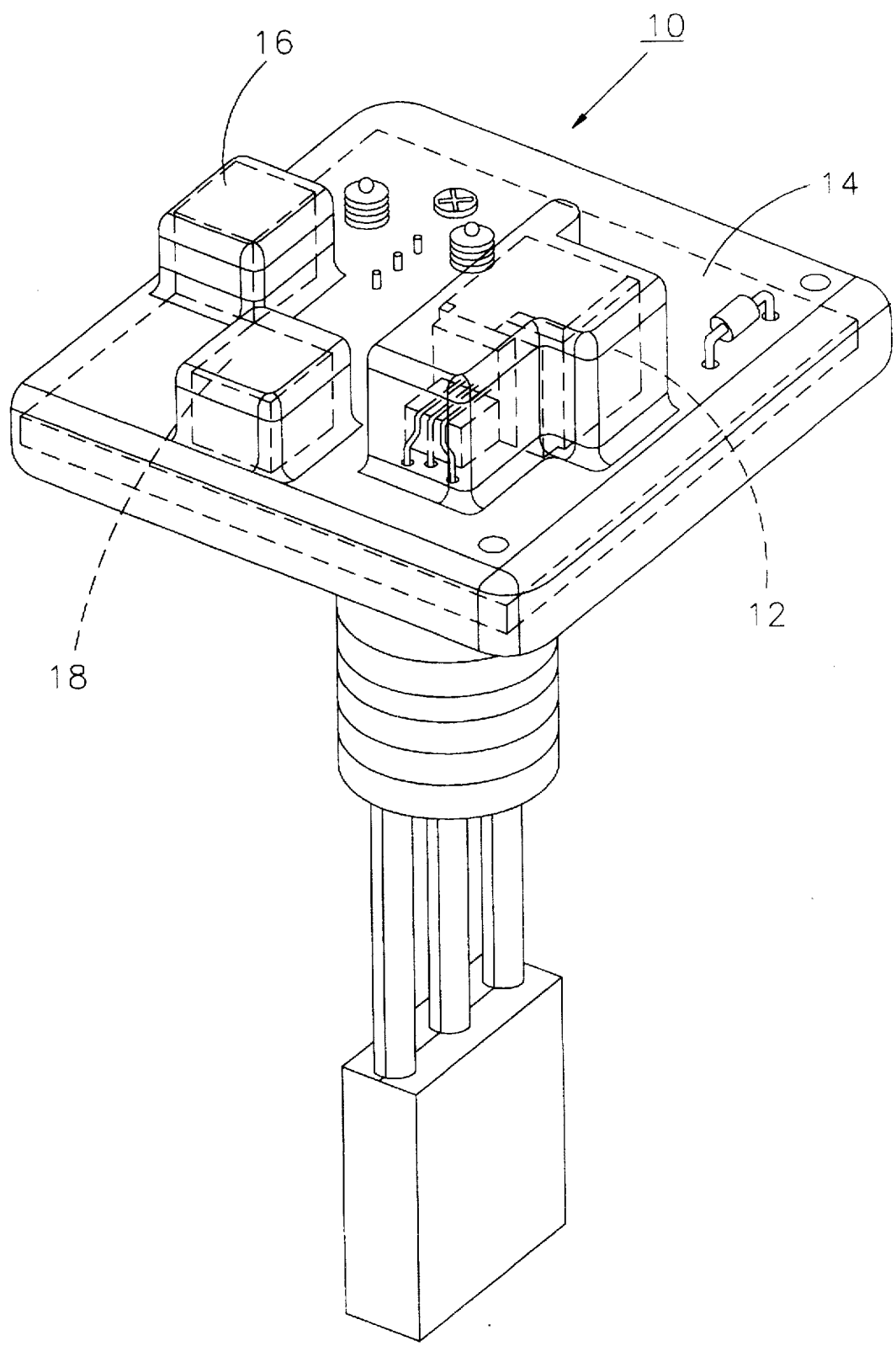
FIG. 1 illustrates a known type of turbidity sensor that can be tested with the present invention.

Throughout the Description of the Preferred Embodiment, like components will be identified by like reference numerals.

The primary purpose of the present invention is to permit turbidity sensors to be tested in a rapid and accurate manner without requiring the turbidity sensors to be immersed in a liquid that has been prepared to have a preselected turbidity. In addition, the present invention was developed in order to permit this rapid and accurate testing of turbidity sensors while also preserving the traceability of the testing procedure to a known and widely accepted standard for turbidity testing.

The present invention will be described in terms of its application to a particular turbidity sensor that measures both transmitted and scattered light. FIG. 1 illustrates a turbidity sensor of this general type which is known to those skilled in the art and described in detail in U.S. Pat. Nos. 5,444,531 and 5,446,531. The structure and operation of the turbidity sensor 10 shown in FIG. 1 are described in significant detail in these two referenced patents. In turbidity sensors of this type, a light source 12 is positioned on a substrate 14 in such a way that it emits light in the direction represented by arrow E. A first light sensitive component 16 is disposed to receive light that is transmitted directly from the light source 12 in the direction represented by arrow T. In certain types of turbidity sensors, a second light sensitive component 18 is disposed at a position to receive light that is scattered by particulate matter in a medium in the direction represented by arrow S in FIG. 1. In a typical application of the turbidity sensor 10, it is submerged within a fluid in a manner that permits the fluid to flow through the open area defined, on three sides, by the faces of the pedestal portions of the turbidity sensor in which the light source 12, the first light sensitive component 16 and the second light sensitive component 18 are contained.

Figure 2:
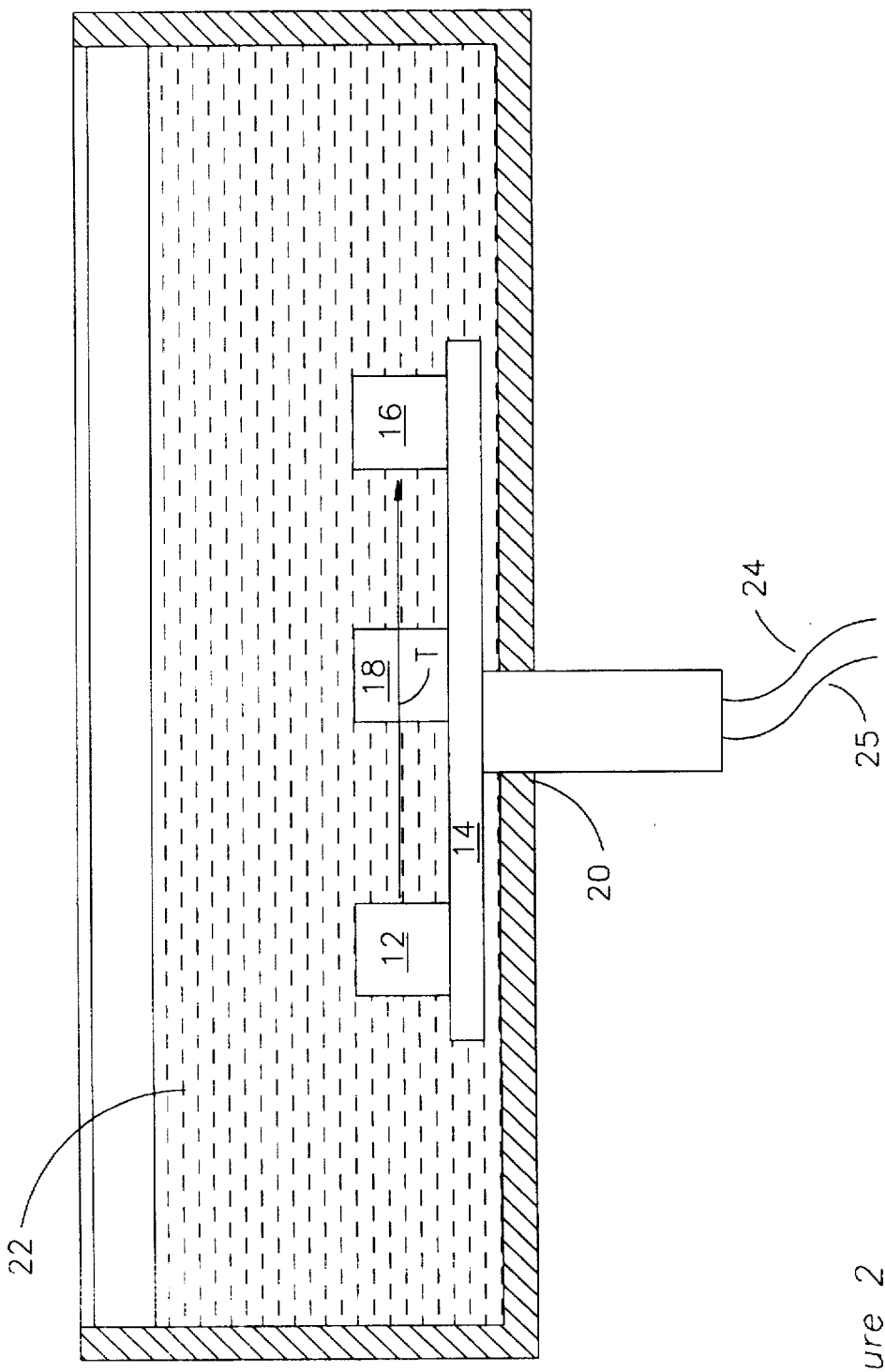
FIG. 2 shows a known method for testing a turbidity sensor such as the one shown in FIG. 1.

FIG. 2 shows a method by which the accuracy and calibration of the turbidity sensor shown in FIG. 1 can be measured. The turbidity sensor can be placed within a vessel 20 and an appropriate solution 22 of liquid can be placed in the vessel. If the solution 22 is properly prepared according to standardized methods to provide a known and precisely determined turbidity of the liquid and if all stray light is prevented from affecting the measurement, the turbidity sensor can be activated and output signals can be received through lines 24 and 25. The output signal received from the turbidity sensor is expected to be accurately representative of the turbidity of the solution in the vessel. The accuracy of the turbidity sensor can then be determined by comparing its output signal to the actual known turbidity of the solution 22. In a typical turbidity sensor, the output signal is some value that is correlated to a turbidity value. Although turbidity is generally measured in NTU's or FTU's, the output signal from a turbidity sensor is generally a value that can be converted to the standard turbidity measurement units. For example, one known technique measures the ratio of the light signal received by the second light sensitive component 18 to the light signal received by the first light sensitive component 16. If the appropriate gain values are chosen for the amplifiers associated with the first and second light sensitive components, the ratio of the two signal from the first and second light sensitive components can be used as an appropriate representation of the actual turbidity of the solution 22.

It can easily be realized that a testing procedure that requires the submersion of the turbidity sensor in a prepared liquid solution, as represented in FIG. 2, is both time consuming and costly if performed on each turbidity sensor that is manufactured in a production line system. In addition, testing procedures of this type make it difficult to maintain clean conditions in the test station area. Furthermore, the precise turbidity level of the liquid solutions are extremely difficult to maintain at a constant preselected magnitude because the solutions tend to settle and, in some cases, the dissolved powder can undergo chemical changes that adversely affect the turbidity of the liquid solution. In addition, certain powders used to product turbidity sample solutions have been determined to be carcinogenesis. The present invention represents an improvement on the testing procedure shown in FIG. 2.

Figure 3:
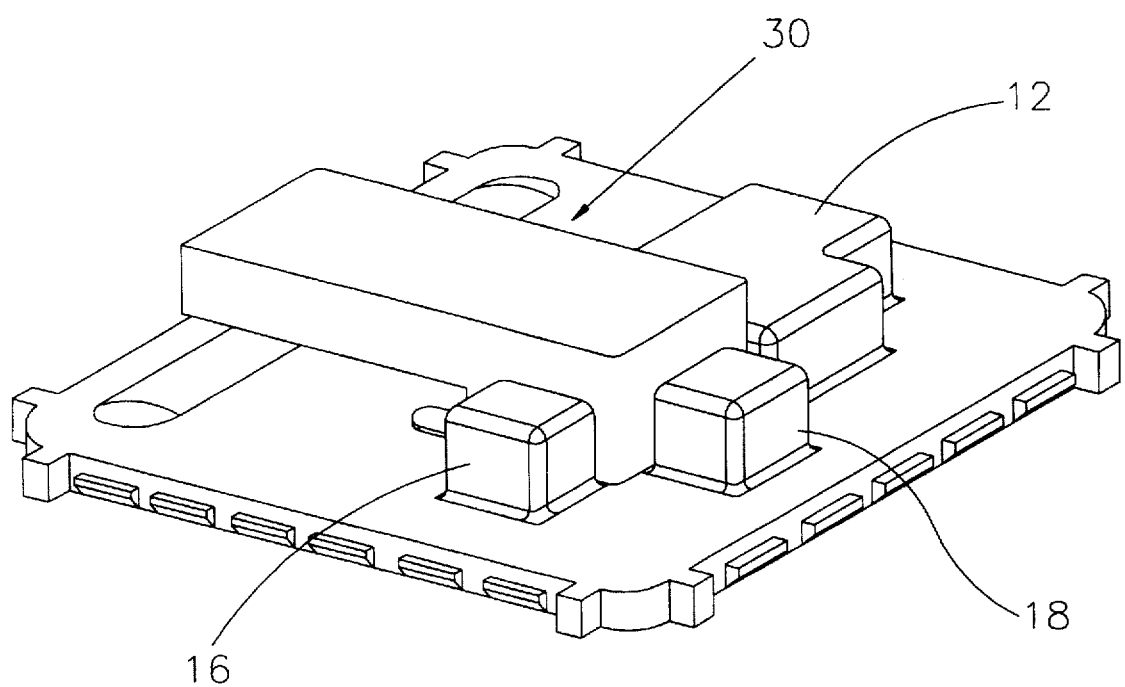
FIG. 3 illustrates a solid block made in accordance with the present invention and disposed within the sensing region of a turbidity sensor.

FIG. 3 shows a solid block 30 that is partially transparent and which is specifically prepared to have a turbidity value within a preselected range. The block 30 is shaped to permit its insertion into the region between the light source 12 and the first and second light sensitive components, 16 and 18. With the block 30 inserted in the region between the light source and the light sensitive components, the turbidity sensor can be activated to provide a signal representing the turbidity of the medium in the sensing position. Assuming that stray light from external sources is prevented from adversely affecting the first and second light sensitive components, the known turbidity of the solid block 30 can be used to test the proper operation of the turbidity sensor and determine whether or not it is providing acceptably accurate information. The use of a solid block 30 allows the sensor to be tested rapidly and also provides a high level of consistency since it is not expected that the turbidity of the solid block 30 will easily change over time.

The use of a solid block 30 provides significant advantages for the testing of turbidity sensors, but it is very important that the turbidity of the block 30 be traceable to the known and accepted turbidity standards used by those skilled in the art. The mere provision of a block 30 with a turbidity value is insufficient for several reasons. First, most turbidity sensors are intended for use in the measurement of turbidity of a liquid during their normal operation. Since the present invention uses a solid block 30 to simulate the measurement of a liquid's turbidity, some means must be provided to determine the actual equivalent turbidity of a liquid that is disposed between the light source 12 and the light sensitive components, 16 and 18. Secondly, the turbidity of the solid block 30 must be within a predetermined range in order to satisfy certain customer requirements regarding the testing and calibration of the turbidity sensor. For example, it is typically expected that a customer would prescribe that the turbidity sensor be tested at certain values of turbidity to make sure that the overall accuracy of the turbidity sensor is known for a range of possible turbidity values of a liquid to be measured. Therefore, it is typically required that the turbidity sensors be tested to assure that they work properly at a certain number of predefined turbidity magnitudes. For example, it is possible that a customer would require that each turbidity sensor be tested at a turbidity magnitude of 1500–1700 NTU's and at another turbidity magnitude of the equivalent of clear water. In many applications of turbidity sensors, the use of two points within the range of possible turbidities that the sensor will encounter is sufficient to appropriately characterize its operation as being acceptable or unacceptable.

The solid block 30 shown in FIG. 3 is manufactured by mixing 8.0 grams of calcium carbonate and 4.99 pounds of clear acrylic powder. The mixture is then melted and molded into the desired shape. Although not specifically illustrated in FIG. 3, the extended leg at the upper portion of the block can be provided with mounting holes that allow the block to be attached to an actuator that moves the block into and out of the region between the light source and the light sensitive components. In addition, the block 30 can be shaped to fit into the opening between these components of the turbidity sensor and avoid certain obstructions that may exist in that region. It has been determined that a mixture of calcium carbonate and clear acrylic, as described above, will produce a solid block having a turbidity within a desired range of 1400-1700 NTU's. Naturally, if other turbidity ranges are desired, the proportions of calcium carbonate and clear acrylic can be appropriately adjusted.

When the solid block 30 is made, it will have a turbidity value that is likely to be within the desired range, but the precise magnitude of the turbidity of the solid block 30 may vary from one block to another because of the normal variations in a mixture of this type and the normal tolerances associated with any manufacturing procedure. Therefore, it is important to characterize the block in association with some known and accepted standard of turbidity measurement.

The method of the present invention initially selects a plurality of turbidity sensors that are then used as sample sensors during further steps of the method. The sample sensors are first checked to make sure that they are all operating in an acceptable manner and able to provide an output signal representative of the turbidity of a medium disposed in their sensing regions. In a preferred embodiment of the present invention, six turbidity sensors are initially selected as the sample sensors.

Figure 4:
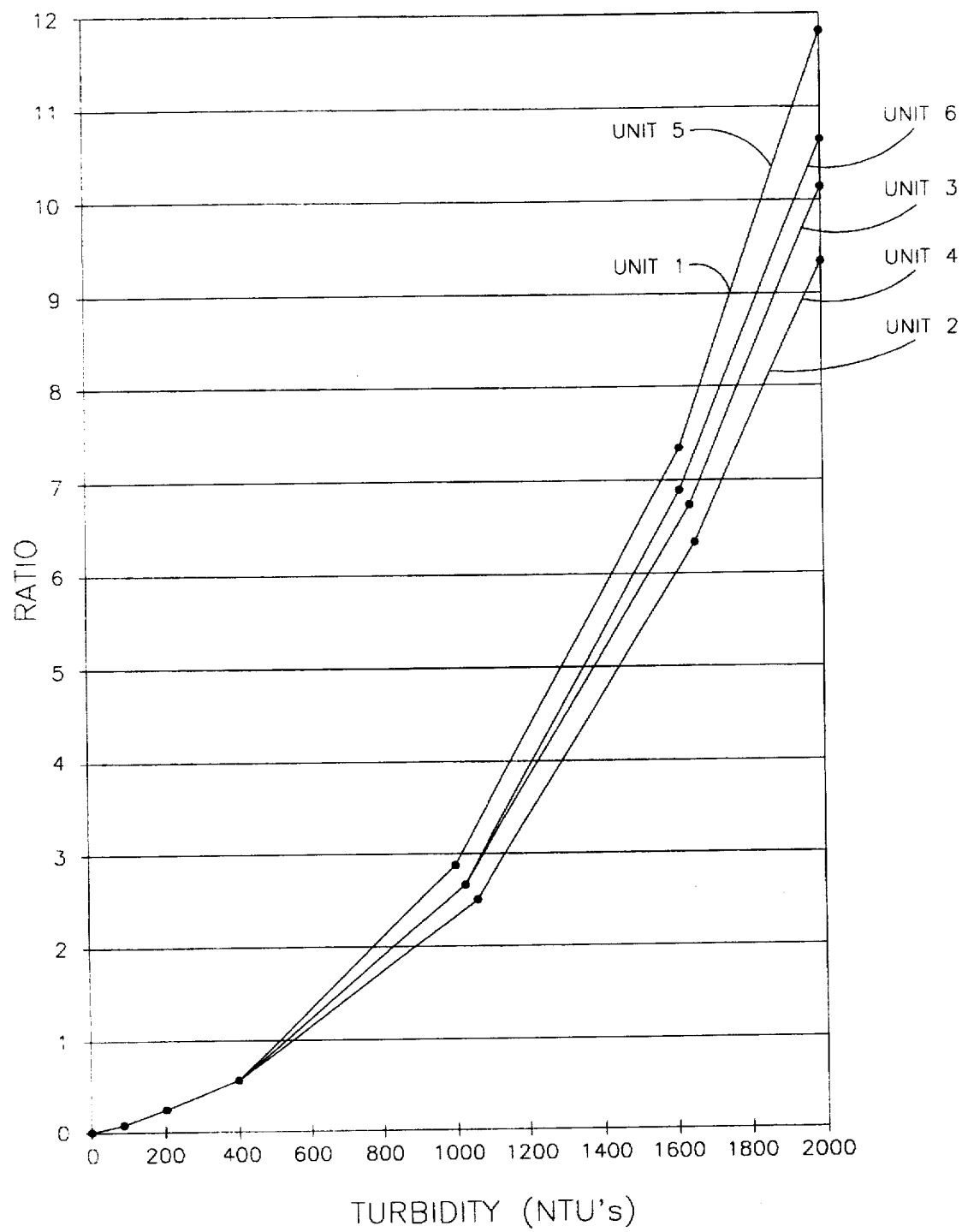
FIG. 4 shows characterization data graphically represented to illustrate the output signal of the six sample sensors as a function of the turbidity of a liquid solution.

Using Formazin, seven liquid solutions are prepared. The seven solutions are mixed in the appropriate proportions of Formazin and distilled water to provide turbidity values of 2000 NTU, 1600 NTU, 1000 NTU, 400 NTU and 100 NTU. In addition, a sample of pure distilled water is used to represent 0 NTU. The six sample sensors are then used to test each of the seven sample solutions. When performing this step of the process, each solution can be measured a plurality of times by each individual sample sensor and the numeric average of the results can be used. However, it should be understood that this is not a requirement in all embodiments of the present invention. Table I shows a typical example of the results achieved during this portion of the process. The sample sensors, which are identified as UNIT1, UNIT2, etc., are shown in Table 1 with their ratio values that were determined during the measurement of the turbidities for the seven liquid samples. These results are graphically represented in FIG. 4. The graphical illustration in FIG. 4 shows that all six of the sample sensors exhibit a generally similar behavior in response to the testing of the seven samples. Ideally, all six sample sensors would provide identical ratio outputs for each of the seven solutions, but it is not unexpected that normal manufacturing processes and component tolerances will result in a slight variation as shown in Table I and FIG. 4.

TABLE I

| TURBIDITY | UNIT1 | UNIT2 | UNIT3 | UNIT4 | UNIT5 | UNIT6 |
|---|---|---|---|---|---|---|
| 0 | 0.02 | 0.03 | 0.03 | 0.03 | 0.03 | 0.03 |
| 100 | 0.08 | 0.08 | 0.11 | 0.09 | 0.09 | 0.09 |
| 200 | 0.18 | 0.17 | 0.21 | 0.19 | 0.2 | 0.19 |
| 400 | 0.49 | 0.47 | 0.51 | 0.47 | 0.51 | 0.49 |
| 1000 | 2.77 | 2.58 | 2.78 | 2.58 | 2.79 | 2.65 |
| 1600 | 7.24 | 6.46 | 6.89 | 6.48 | 7.28 | 6.96 |
| 2000 | 11.17 | 9.68 | 10.23 | 9.67 | 11.2 | 10.57 |

The process described above in conjunction with Table I and FIG. 4 serves a valuable purpose. It provides information regarding the magnitude of the ratio output signal provided by all six of the sample sensors when used to measure the turbidity of a specific liquid sample having a turbidity in the range of 1400-1700 NTU's.

Figure 5:
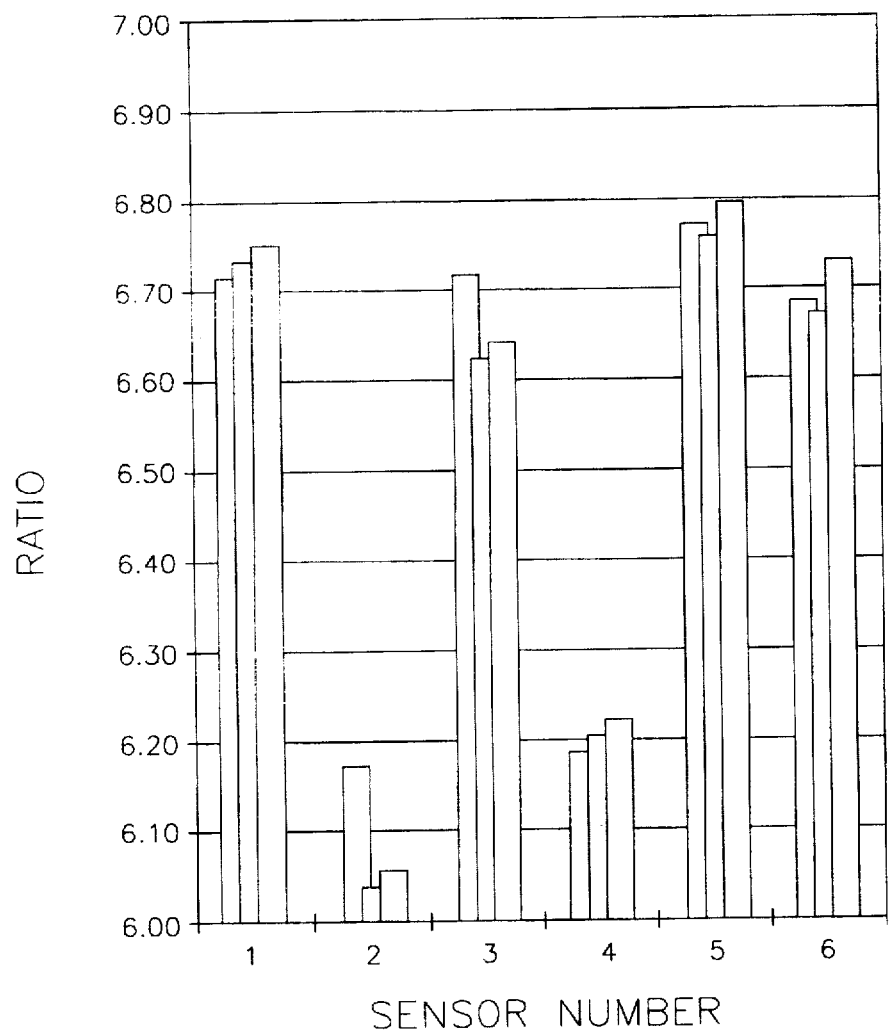
FIG. 5 is a graphical representation of the three trial measurements of the turbidity of a solid block made by six sample sensors.

The next step is to place the solid block 30 in the position shown in FIG. 3 and operate each of the six sample turbidity sensors a plurality of times to provide a first representative magnitude of the ratio that each of the six sample sensors determines when measuring the turbidity of the solid block 30. Table II shows the results of this process step. Each of the six sample sensors is used to take three independent readings when the solid block 30 is disposed in its sensing region. For each sample sensor, the three trials are averaged as shown. These results are graphically represented in the bar chart of FIG. 5. As can be seen in Table II and in FIG. 5, each of the six sensors provides a slightly different response when used to measure the turbidity of the solid block 30.

TABLE II

| SENSOR NUMBER | TRIAL 1 | TRIAL 2 | TRIAL 3 | AVG |
|---|---|---|---|---|
| 1 | 6.74 | 6.75 | 6.76 | 6.75 |
| 2 | 6.17 | 6.05 | 6.07 | 6.10 |
| 3 | 6.71 | 6.62 | 6.65 | 6.66 |
| 4 | 6.19 | 6.20 | 6.22 | 6.20 |
| 5 | 6.78 | 6.77 | 6.80 | 6.78 |
| 6 | 6.68 | 6.67 | 6.72 | 6.69 |

Figure 6:
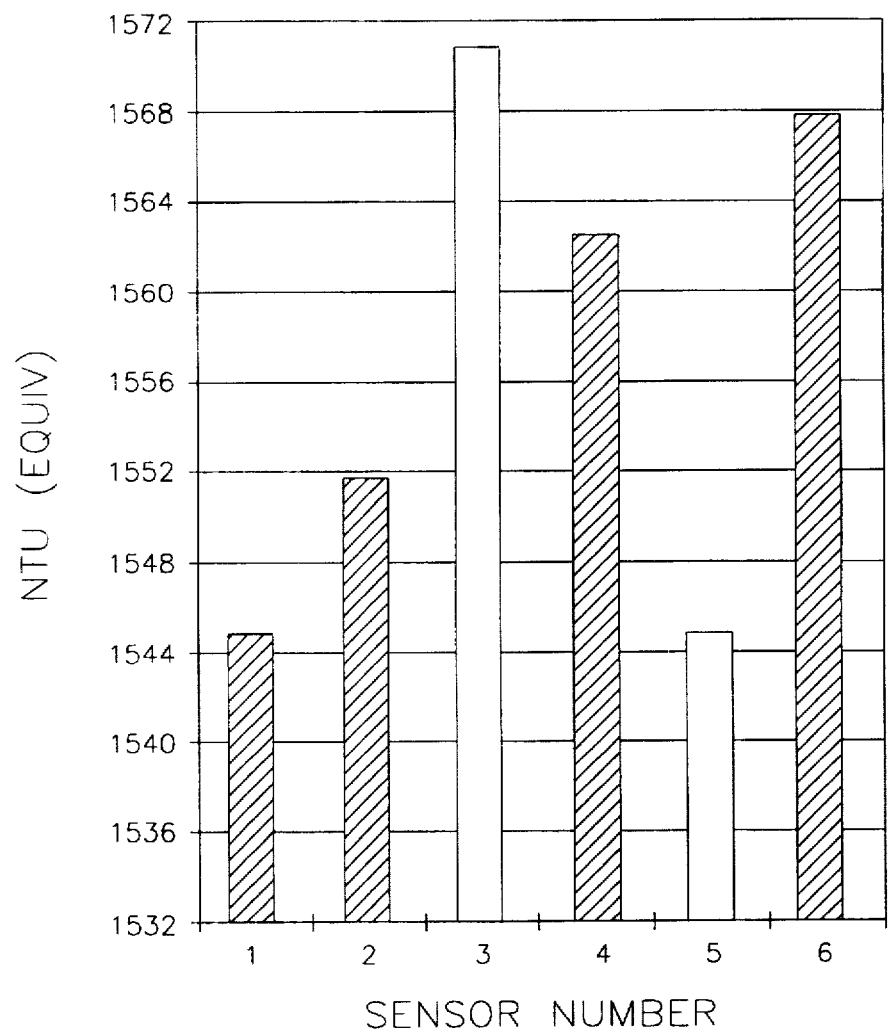
FIG. 6 is a graphical representation which shows the average values for the six sample sensors illustrated as equivalent NTU magnitudes.

Using the characterization data obtained in conjunction with the process step described above in relation to Table I and FIG. 4, the equivalent NTU magnitude is determined for each of the six sample sensors based on the average ratio achieved during the three trials described above in conjunction with Table II and FIG. 5. Table III shows the average ratio value, or first representative magnitude, for each of the six sample sensors. In addition, Table III also shows the NTU equivalent for the obtained ratio value, based on the characterization shown in FIG. 4 for each of the six sample sensors. Using the NTU equivalent value, the highest and lowest sample sensors are deleted from the list. These results are also shown in FIG. 6. Based on the NTU equivalent magnitudes shown in Table III and illustrated by the bar chart of FIG. 6, the third sample sensor has the highest NTU value and the fifth sample sensor has the lowest NTU value when tested with the solid block 30 shown in FIG. 3. The values for the third and fifth sample sensors are ignored during the remaining steps of the procedure. The first representative magnitude, or average ratio, for the first, second, fourth and sixth sensors are then averaged to determine a second representative magnitude. This procedure is done for the values obtained by the four selected sample sensors when testing both the solid block 30 and air as represented by the absence of all media within the sensing region of the sensors except air and with all ambient light being blocked from affecting the operation of the turbidity sensor.

TABLE III

| SENSOR NUMBER | NTU EQUIV | AVG RATIO |
|---|---|---|
| 1 | 1545 | 6.75 |
| 2 | 1552 | 6.16 |
| 3 | 1571 | 6.66 |
| 4 | 1563 | 6.20 |
| 5 | 1545 | 6.78 |
| 6 | 1568 | 6.69 |

The second representative magnitude, which is calculated by averaging the average ratios shown in Table III for the first, second, fourth and sixth sample sensors, represents the average NTU magnitude that would be expected to be achieved if the four chosen sample sensors were used to measure a liquid solution that was specifically prepared to have a turbidity value of 1557 which is the average NTU equivalent magnitude for the first, second, fourth and sixth sample sensors shown in Table III. In other words, the results indicated in Table III and FIG. 6 indicate that a typical turbidity sensor would be expected to provide an output signal representing a ratio magnitude of 6.435 when used to test the solid block 30 shown in FIG. 3. The average ratio for the first, second, fourth and sixth sample sensors yield an average magnitude of 6.435. This is the second representative magnitude that is used during the production testing of mass produced turbidity sensors. Naturally, a tolerance band is also provided for both the solid block turbidity reading and the air turbidity reading to allow for minor variations due to the potential variability of manufacturing and the component tolerances relating to each of the mass produced turbidity sensors. Although not specifically shown in Table III or the figures, it should be understood that each of the six sample sensors also is associated with an average ratio for the measurement that is made with only air within the sensing region of the turbidity sensor. Those average ratios are associated with each of the six sample sensors. These average ratio values are used to provide the first representative magnitude, relating to the measurement of air within the sensing region for each sensor, and are averaged for the first, second, fourth and sixth sensors to determine the second representative magnitude that will be used in the production testing of turbidity sensors. The only difference between the treatment of the numerical values for the air testing step, compared to the solid block testing step, is that the values obtained during the air testing step are not used in the selection process whereby the third and fifth sensors are eliminated. In other words, the elimination step uses only the values obtained during the testing of the solid block and the eliminations decided during that step are effective when calculating the second representative magnitude for the air testing step. Table IV shows the actual results of a typical procedure that yields three trial magnitudes for each of the six sample sensors and for both a no media test, or air test, and a media test using the solid block 30 shown in FIG. 3.

TABLE IV

| | TURBIDITY SENSOR RATIO OUTPUT | | | | | |
|---|---|---|---|---|---|---|
| | NO MEDIA RATIO OUTPUT | | | MEDIA RATIO OUTPUT | | |
| SENSOR NUMBER | TRIAL 1 | TRIAL 2 | TRIAL 3 | TRIAL 1 | TRIAL 2 | TRIAL 3 |
| 1 | .17 | .17 | .17 | 6.74 | 6.75 | 6.76 |
| 2 | .17 | .16 | .16 | 6.17 | 6.05 | 6.07 |
| 3 | .17 | .17 | .17 | 6.71 | 6.62 | 6.65 |
| 4 | .16 | .16 | .16 | 6.78 | 6.77 | 6.8 |
| 5 | .16 | .16 | .16 | 6.68 | 6.67 | 6.72 |
| 6 | .18 | .18 | .18 | 6.68 | 6.67 | 6.72 |

The procedures described above in conjunction with the method of the present invention allow a rapid and accurate testing procedure to be implemented by using a solid block rather than using liquid solutions to test turbidity sensors. The steps of the method are planned to provide traceability to actual liquid turbidity samples. In summary, the method comprises the step of selecting six sample turbidity sensors to be used as a standard for calibrating and characterizing the solid block. Liquid solutions are prepared to have turbidities of 0 NTU, 100 NTU, 200 NTU, 400 NTU, 1000 NTU, 1600 NTU and 2000 NTU. Three readings are taken for each sensor in each of the liquid solutions. The six sample sensors are then characterized to describe the output signal for each of the sample sensors as a function of the NTU of the liquid being measured. Then, the solid block is measured by each of the six sample sensors three times to determine the average ratio value and the corresponding average NTU value for each of the six sensors when measuring the solid block. Air is also measured by each sensor and repeated to achieve three values. The four sample sensors having the central magnitudes are selected by ignoring the results of the two sample sensors having the highest and lowest output signal for the solid block test. The four ratio values for the four selected sample sensors are averaged to provide a second representative magnitude for both the solid block test and the air test. Upper and lower tolerances are selected for both the solid block and air tests. Using the tolerance band determined above, production turbidity sensor units are tested with air and with the solid block to determine whether or not they provide output signals that are within the two predetermined tolerance bands.

Although the present invention has been described in particular detail and illustrated to specifically show a most preferred embodiment, it should be understood that alternative steps could be substituted without changing the overall character of the present invention.

The embodiments of the invention in which an exclusive property or right is claimed are defined as follows:

1. A method for testing a turbidity sensor, comprising:
   providing a solid block of material having a preselected turbidity;
   disposing said solid block between a light source of said turbidity sensor and a first light sensitive component of said turbidity sensor;
   activating said turbidity sensor to provide an output signal which is representative of the turbidity of a medium disposed between said light source and said first light sensitive component;
   receiving an output signal from said turbidity sensor;
   comparing said output signal to a predetermined range of values;
   determining the acceptability of said turbidity sensor based on said comparing step; and
   characterizing said preselected turbidity of said solid block by testing a plurality of sample sensors, said characterizing step further comprising the steps of:
   selecting said plurality of sample sensors;
   disposing said solid block between a light source and a first light sensitive component of each of said sample sensors;
   sequentially activating each of said sample sensors to provide said output signal from each of said sample sensors;
   receiving said output signal from each of said sample sensors;
   determining a plurality of first representative magnitudes of said output signal, one for each of said sample sensors;
   calculating a second representative magnitude as a function of said plurality of first representative magnitudes; and
   calculating said predetermined range of values as a function of said second representative magnitude.

2. The method of claim 1, further comprising:
   providing a plurality of liquid samples, each of said liquid samples being of a measurably different turbidity than that of the other of said plurality of liquid samples; and measuring the turbidity of each of said plurality of liquid samples with each of said sample sensors prior to said characterizing step.

3. The method of claim 1, wherein:

said turbidity sensor comprises said light source, said first light sensitive component and a second light sensitive component.

4. The method of claim 3, wherein:

said disposing step comprises the step of disposing said solid block at a location between said light source and said first light sensitive component and between said light source and said second light sensitive component.

5. The method of claim 4, wherein:

said second representative magnitude is calculated by ignoring the highest and lowest ones of said plurality of first representative magnitudes and averaging the remaining ones of said plurality of first representative magnitudes.

6. The method of claim 1, wherein:

said solid block comprises a quantity of calcium carbonate mixed within a matrix of acrylic.

7. A method for testing a turbidity sensor, comprising:

providing a solid block of material having a preselected turbidity;

disposing said solid block between a light source of said turbidity sensor and a first light sensitive component of said turbidity sensor;

activating said turbidity sensor to provide an output signal which is representative of the turbidity of a medium disposed between said light source and said first light sensitive component;

receiving an output signal from said turbidity sensor;

comparing said output signal to a predetermined range of values;

determining the acceptability of said turbidity sensor based on said comparing step; and characterizing said preselected turbidity of said solid block by testing a plurality of sample sensors, said turbidity sensor comprising a second light sensitive component, said disposing step comprising the step of disposing said solid block at a location between said light source and said first light sensitive component and between said light source and said second light sensitive component, said characterizing step comprising the steps of:

selecting said plurality of sample sensors;

disposing said solid block between a light source and a first light sensitive component of each of said sample sensors;

sequentially activating each of said sample sensors to provide said output signal from each of said sample sensors;

receiving said output signal from each of said sample sensors;

determining a plurality of first representative magnitudes of said output signal one for each of said sample sensors;

calculating a second representative magnitude as a function of said plurality of first representative magnitudes; and calculating said predetermined range of values as a function of said second representative magnitude.

8. The method of claim 7, further comprising:

providing a plurality of liquid samples, each of said liquid samples being of a measurably different turbidity than that of the other of said plurality of liquid samples; and measuring the turbidity of each of said plurality of liquid samples with each of said sample sensors prior to said characterizing step.

9. The method of claim 8, wherein:

said second representative magnitude is calculated by ignoring the highest and lowest ones of said plurality of first representative magnitudes and averaging the remaining ones of said plurality of first representative magnitudes.

10. The method of claim 9, wherein:

said solid block comprises a quantity of calcium carbonate mixed within a matrix of acrylic.

* * * * *